United States Patent
Udell et al.

(10) Patent No.: US 6,855,733 B2
(45) Date of Patent: Feb. 15, 2005

(54) FORMULATION AND MANUFACTURING PROCESS FOR COENZYME Q10 SOFT GEL CAPSULES

(75) Inventors: Ronald G. Udell, Beverly Hills, CA (US); Yousry M. A. Naguib, Arcadia, CA (US); Siva P. Hari, Riverside, CA (US)

(73) Assignee: Soft Gel Technologies, Inc., Los Angeles, CA (US)

( * ) Notice: Subject to any disclaimer, the term of this patent is extended or adjusted under 35 U.S.C. 154(b) by 0 days.

(21) Appl. No.: 10/368,260

(22) Filed: Feb. 18, 2003

(65) Prior Publication Data
US 2003/0157083 A1 Aug. 21, 2003

Related U.S. Application Data

(63) Continuation-in-part of application No. 09/873,156, filed on Jun. 1, 2001, now abandoned.
(60) Provisional application No. 60/263,953, filed on Jan. 24, 2001.

(51) Int. Cl.$^7$ .............................................. A61K 31/20
(52) U.S. Cl. ...................... 514/560; 514/962; 424/451; 424/452; 424/456
(58) Field of Search .................. 424/451, 452, 424/456; 514/560, 962

(56) References Cited

U.S. PATENT DOCUMENTS

| | | |
|---|---|---|
| 4,824,669 A | 4/1989 | Folkers et al. |
| 5,500,416 A | 3/1996 | Miyazawa et al. |
| 6,020,383 A | 2/2000 | Stone et al. |
| 6,054,136 A | 4/2000 | Farah et al. |
| 6,069,167 A | 5/2000 | Sokol |
| 6,203,818 B1 | 3/2001 | Vester |
| 6,365,181 B1 * | 4/2002 | Matthews ................. 424/451 |
| 6,545,184 B1 | 4/2003 | Lipshutz |
| 6,616,942 B1 | 9/2003 | Udel |

FOREIGN PATENT DOCUMENTS

| | | |
|---|---|---|
| DE | 3512054 | 10/1986 |
| EP | 0 888 774 | 1/1999 |

OTHER PUBLICATIONS

R. Chopra et al, "A New Coenzyme Q10 Preparation with Enhanced Bioavailability", FASEB Journal, 11 (3), pp. A586, 1997, Abstract.

M. Weis, et al., "Bioavailability of Four Oral Coenzyme Q10 Formulations in Healthy Volunteers", Molec. Aspects. Med., vol. 15, (Supplement) pp. s273–s280, 1994.

http://www.pformulate.com/pformsoftgel.htm.

* cited by examiner

Primary Examiner—Jean C. Witz
(74) Attorney, Agent, or Firm—Scott D. Rothenberger; Dorsey & Whitney LLP

(57) ABSTRACT

A soft gelatine capsule formulation for improved manufacturing of Coenzyme Q10, comprising Coenzyme Q10 in a thixatropic gelatine carrier capable of admixing without heating with Coenzyme Q10, and capable of keeping Coenzyme Q10 in suspension at ambient temperature.

18 Claims, No Drawings

FORMULATION AND MANUFACTURING PROCESS FOR COENZYME Q10 SOFT GEL CAPSULES

This is a Continuation-in-Part of U.S. application Ser. No. 09/873,156 which was filed Jun. 1, 2001, now abandoned, that in turn claims priority benefit of U.S. Provisional Application Ser. No. 60/263,953 filed Jan. 24, 2001, the contents of which are incorporated herein in their entirety.

BACKGROUND OF THE INVENTION

1. Field of the Invention

This invention relates to a composition and process of manufacturing Coenzyme Q10 with improved human absorption characteristics in a thixatropic gelatin carrier capable of admixing without heating the Coenzyme Q10, and capable of suspending Coenzyme Q10 in a uniform dispersion.

2. Background of the Invention

Coenzyme Q10 (CoQ10 or Ubiquinone) is a large molecular weight (863.63 grams) lipid compound that is produced in the liver and perhaps other body organs. The total human body content is estimated to be 1.4 to 1.8 grams, depending on the age and the physical fitness of the individual. Although CoQ10 is found in the mitochondria and other organelles of every living cell, it appears to be most abundant in tissues with a high number of mitochondria and a high level of metabolic activity. For example, there is approximately 4 mg of CoQ10 in the heart tissues, and about 1000 mg in the skeletal muscle. The blood acts as a CoQ10 reservoir and transport media between endogenous CoQ10 synthesis in the liver, exogenous COQ10 absorption from digested food substances in the intestinal tract, and the body cells. Endogenous synthesis appears to be responsible for 56 percent and exogenous sources for 44 percent of the body's CoQ10 requirements. These numbers are currently being studied and endogenous CoQ10 synthesis may be significantly deficient in the elderly. Furthermore, certain disease states, such as mitochondrial myopathy, and prescription drugs, such as cholesterol-lowering statin drugs, seem to deplete the endogenous CoQ10 levels in the body. These deficiencies are not related to the total caloric intake, but rather to the vitamin content of ingested foods as the body requires multiple vitamins for the synthesis of CoQ10.

CoQ10 requirements of the body are also variable between individuals and are dependent on age, physical activity, and disease. It is estimated that the body CoQ10 utilization is between 5 and 9 mg per day. Intercellular CoQ10 is required for the synthesis of energy and therefore essential for life. Energy synthesis occurs in the mitochondria, where CoQ10 provides an electron for the electron transport chain in the cytochrome system, in which adenosine triphosphate (ATP) is synthesized. As CoQ10 gives up an electron for the ATP synthesis, it gets oxidized. If CoQ10 is used as an antioxidant, it gets oxidized and is no longer available to provide electrons and function in the synthesis of ATP. Under conditions of high metabolic stress, endogenous sources may become inadequate to meet the body's CoQ10 requirement for ATP synthesis. Under such conditions, dietary CoQ10 supplementation has been shown to be an effective source. CoQ10 has been used to treat heart failure, chronic fatigue and patients with psoriasis and planter warts. In all cases, it has been found that the improved soft gel formulation, at doses of 30–100 mg/day of CoQ10, have been proven to be superior to commercially available 60 mg dry powder capsules, and existing 100 mg/day CoQ10 soft gel formulations.

An appropriate CoQ10 dosage for a normal individual compared to the dosage necessary for a diseased individual has been difficult to ascertain. Recommended doses of 10 to 30 mg/day were found to be ineffective for patients with significant CoQ10 deficiencies. In the past 15 years, it has become generally accepted that poor intestinal absorption of certain CoQ10 formulations limits their effective use. For this reason, 50 and 150 or even 200 mg tablets or capsules are commercially available to the consumer, at a considerable higher cost, the main cost driver being the CoQ10.

Folkers et al. (U.S. Pat. No. 4,824,669) addresses a soft gel capsule with CoQ10 and at least one vegetable oil. This formulation was determined to increase blood CoQ10 levels to 2.5 $\mu$g/ml compared to 1.6 $\mu$g/ml for an equivalent 100 mg dose of dry powder COQ10. Many different CoQ10 formulations have appeared which are claimed to increase intestinal absorption. However, intestinal absorption data, collected under near basal conditions, which compare CoQ10 alone in oil with dry powder CoQ10, are inconclusive.

SUMMARY OF THE INVENTION

The present invention comprises a formulation of Coenzyme Q10 for improved manufacturing of soft gelatine capsules containing Coenzyme Q10.

According to the present invention, a preferred soft gel formulation includes Coenzyme Q10, Vitamin E (mixed tocopherols) added as a functional antioxidant, and a thixatropic gelatin carrier which has the ability of enhancing the solubility and stability of the active ingredient and provides for better absorption thereof in humans. An additional ingredient, an antioxidant, either from natural or synthetic sources, can be added in order to prepare a potent combination antioxidant formulation. The preferred soft gel Coenzyme Q10 formulation is administered twice a day in dosages of about 30 mg, thereby reducing the Coenzyme Q10 cost while producing the desired retained Coenzyme Q10 in the human body.

Other features and advantages of the present invention will become more apparent from the following detailed description, which illustrate, by way of example, the principles of the invention.

DETAILED DESCRIPTION OF THE PREFERRED EMBODIMENTS

The present invention utilizes a gelatine carrier with thixatropic properties and substantial capacity to suspend active ingredients in a uniform dispersion. The carrier composition used in the present invention is described in U.S. Pat. No. 6,365,181 (issued to Matthews), and is a thixatropic carrier gel comprising a homogeneous dispersion of viscosity modifiers and surface active agents in vegetable oil. When the carrier composition is agitated, such as by slow stirring, it becomes fluid, and when the agitation is stopped, it becomes a highly viscous semi-solid. Active agents are easily admixed with the carrier composition by stirring and high loadings of the active agents can be used to make a stable uniform dispersion within the carrier composition because the composition becomes semi-solid when stirring is stopped.

As described in the Matthews patent, the components of the carrier composition include from about 84% to 95% of a vegetable oil, from about 1% to 9% of a viscosity modifier, and from about 1% to 15% of a surface active agent such that the total amounts to 100%. Other details of the thixatropic gelatine carrier used in the present invention are described in the Matthews patent, and are incorporated herein by reference.

The unique formulation of the present invention involves the following sequence of ingredients and process methodology:

(A) Heat the thixatropic gelatine carrier to a temperature of about 25° C. to about 35° C. (preferably about 27° C. to about 30° C.);

(B) Simultaneously add in a container under vacuum the following ingredients to the pre-heated thixatropic gelatine carrier: Coenzyme Q10, Vitamin E, and if desired, additional antioxidant in compatible form, the vacuum being to prevent oxidation of any of the ingredients;

(C) Blend and continuously stir all of the ingredients into a mixture;

(D) Cool the mixture to a temperature of about 23° C. to 28° C. (preferably about 25° C.);

(E) Mix the mixture within the container under a blanket of nitrogen gas to prevent oxidation of any of the ingredients; and (F) Encapsulate the mixture in a soft gel capsule.

If the cooled mixture sits for any length of time under its blanket of nitrogen before encapsulation, re-mix under the blanket of nitrogen to assure a homogenous mixture for encapsulation.

Typical amounts of ingredients per capsule are:

50 to 500 mg of the thixatropic gelatine carrier, described above;

30 to 100 mg of Coenzyme Q10;

10 to 100 IU Vitamin E; and if desired 0.5 to 500 mg of additional antioxidant.

The bioavailability or intestinal absorption of CoQ10 has been a major controversy in the international CoQ10 research community. Previous data indicate that only 1 to 3% of a dry powder CoQ10 formulation is absorbed through the lacteals in the intestines and appears in the blood over a twelve hour interval. In general, blood levels of 1.2 to 1.6 $\mu$g/ml have been reported, when taking 30 to 60 mg/day dry powder CoQ10 formulation for 30 days. It has been reported that when a dry powder CoQ10 formulation is taken with a fat, such a peanut butter, steady-state blood levels of 2.0 to 2.8 $\mu$g/ml are measurable. Multiple clinical trials were conducted in the United States and Europe using the Folkers (U.S. Pat. No. 4,824,669) soft gel. With a dosage of 100 mg/day multiple investigators have reported group mean blood levels of 2.3 to 3.5 $\mu$g/ml depending on the laboratory conducting the measurement.

The present invention's 30 mg CoQ10 soft gel formulation of CoQ10 provides approximately 50%, and with two capsules 100%, of the daily CoQ10 requirements of a normal sedentary individual. It would take at least three of the dry powder 30 mg CoQ10 capsules to produce the same effects as one of the present invention in 30 mg soft gel form, and six of the dry powder 30 mg CoQ10 capsules to produce the same effect as two of the present invention 30 mg CoQ10 soft gel capsules.

Regardless of the absorption mechanism, the significantly higher basal blood CoQ10 levels (167%) and the 273% greater absorption rate found in studies, establish that the present invention soft gel formulation is indeed a superior product to the dry powder CoQ10 formulations. This may be especially true for those individuals whose daily COQ10 requirement is elevated due to: high physical activity; a need for CoQ10 as an antioxidant; or active disease associated with known CoQ10 deficiencies.

Cellular CoQ10 content is a function of the number and quality of the cellular mitochondria. For example, the failing heart muscle has 2.2 $\mu$g CoQ10 per mg tissue and a blood CoQ10 deficiency (0.3–0.5 $\mu$g/ml). The normal conditioned heart has 6.3 $\mu$g/gm in its tissue, and a low basal blood level (0.5–0.6 $\mu$g/ml). These results indicate that supplemental CoQ10 enters the cell. This observation has also been reported for skeletal muscles of trained and non-trained athletes.

The subjective and objective responses to supplemental CoQ10 in the normal individual appear more rapidly compared to that of the physically unfit or the diseased individual with a CoQ10 deficiency. The most probable reason for this observation is that the metabolic machinery (mitochondria) is viable in the non-diseased normal volunteer, whereas the mitochondria are atrophied in the cells of de-conditioned and diseased individuals. Therefore, it takes time in the diseased individual to build up the mitochondria to a more normal activity level and to normalize their distribution in the organ system involved.

Thus, there has been described a novel CoQ10 formulation and method of formulation, which fulfill all the objects and advantages sought therefor. Many changes, modifications, variations and applications of the subject invention will become apparent to those skilled in the art after consideration of the specification. All such changes, modifications, alterations and other uses and applications which do not depart from the spirit and scope of the invention are deemed to be covered by the invention which is limited only by the claims that follow.

What is claimed is:

1. A soft gel capsule comprising Coenzyme Q10 in combination with an antioxidant in a thixatropic gelatine carrier thereby providing a stable uniform suspension of Coenzyme Q10.

2. The soft gel capsule of claim 1, wherein the thixatropic gelatine carrier is a semi-solid at a temperature of about 23° C. to about 28° C. and becomes fluid when stirred.

3. The soft gel capsule of claim 1, wherein the thixatropic gelatine carrier is comprised of:

from about 84% to about 95% vegetable oil selected from the group consisting of soybean oil, rapeseed oil, palm oil, and cotton seed oil;

from about 1% to about 9% of a viscosity modifier selected from the group consisting of a glyceryl palmito stearate and glyceryl behenate; and from about 1% to about 15% of a surface active agent comprising polyglyceryl oleate.

4. The soft gel capsule of claim 1, wherein the amount of Coenzyme Q10 in the soft gel capsule ranges from 8 to 40% by weight.

5. The soft gel capsule of claim 1, wherein the amounts of the antioxidant in the soft gel capsule ranges from 1 to 10% by weight.

6. The soft gel capsule of claim 1, wherein the antioxidant is vitamin E.

7. A process of manufacturing a soft gel capsule comprising Coenzyme Q10, said process including:

(a) heating a thixatropic gelatine carrier to a temperature that liquefies the carrier;

(b) blending in a container under vacuum the heated thixatropic gelatine carrier, Coenzyme Q10, and Vitamin E;

(c) cooling the blended mixture to a temperature thereby causing the mixture to be a viscous semi-solid;

(d) mixing the cooled mixture under a nitrogen blanket; and (e) encapsulating the mixed, cooled mixture in a soft gel capsule.

8. The process of claim 7, wherein the thixatropic gelatine carrier is comprised of:

from about 84% to about 95% vegetable oil selected from the group consisting of soybean oil, rapeseed oil, palm oil, and cotton seed oil;

from about 1% to about 9% of a viscosity modifier selected from the group consisting of a glyceryl palmito stearate and glyceryl behenate; and from about 1% to about 15% of a surface active agent comprising polyglyceryl oleate.

9. The process of claim 7, wherein the thixatropic gelatin carrier is heated from about 27° C. to about 30° C.

10. The process of claim 7, wherein 30 to 100 mg of the Coenzyme Q10 and 10 to 100 IU of the Vitamin E are in each capsule.

11. The process of claim 7, wherein the thixatropic gelatin carrier is cooled from about 23° C. to 28° C.

12. The process of claim 7, wherein 50 to 500 mg of the thixatropic gelatin carrier is in each capsule.

13. A soft gel capsule, prepared by a process comprising the steps of:

(a) heating a thixatropic gelatine carrier to a temperature that liquefies the carrier;

(b) blending with the heated thixatropic gelatine carrier, Coenzyme Q10 and Vitamin E;

(c) cooling the blended mixture to a temperature, thereby causing the mixture to form a viscous semi-solid; and (e) encapsulating the mixed, cooled mixture in a soft gel capsule.

14. The soft gel capsule prepared by the process of claim 13, wherein the thixatropic gelatine carrier is comprised of:

from about 84% to about 95% vegetable oil selected from the group consisting of soybean oil, rapeseed oil, palm oil, and cotton seed oil;

from about 1% to about 9% of a viscosity modifier selected from the group consisting of a glyceryl palmito stearate and glyceryl behenate; and from about 1% to about 15% of a surface active agent comprising polyglyceryl oleate.

15. The soft gel capsule prepared by the process of claim 13, wherein the thixatropic gelatin carrier is heated from about 27° C. to about 30° C.

16. The soft gel capsule prepared by the process of claim 13, wherein 30 to 100 mg of the Coenzyme Q10 and 10 to 100 IU of the Vitamin E are in each capsule.

17. The soft gel capsule prepared by the process of claim 13, wherein the thixatropic gelatin carrier is cooled from about 23° C. to 28° C.

18. The soft gel capsule prepared by the process of claim 13, wherein 50 to 500 mg of the thixatropic gelatin carrier is in each capsule.

* * * * *